US00PP19694P2

(12) United States Plant Patent
Misato et al.

(10) Patent No.: US PP19,694 P2
(45) Date of Patent: Feb. 10, 2009

(54) ***MANDEVILLA* PLANT NAMED 'SUNPARACOPAPI'**

(50) Latin Name: *Mandevilla hybrida*
Varietal Denomination: Sunparacopapi

(75) Inventors: Tomoya Misato, Yamanashi (JP); Yasuyuki Murakami, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 12/079,269

(22) Filed: Mar. 25, 2008

(51) Int. Cl.
*A01H 5/00* (2006.01)

(52) U.S. Cl. ..... Plt./232

(58) Field of Classification Search ..... Plt./232
See application file for complete search history.

*Primary Examiner*—Annette H Para
(74) *Attorney, Agent, or Firm*—C. A. Whealy

(57) ABSTRACT

A new and distinct cultivar of *Mandevilla* plant named 'Sunparacopapi', characterized by its upright and vining plant habit; medium-sized foliage; freely flowering habit; pink-colored flowers; and long flowering period.

1 Drawing Sheet

Botanical designation: *Mandevilla hybrida.*
Cultivar denomination: 'Sunparacopapi'.

BACKGROUND OF THE INVENTION

The present invention relates to a new and distinct cultivar of *Mandevilla,* botanically known as *Mandevilla hybrida* and hereinafter referred to by the name 'Sunparacopapi'.

The new *Mandevilla* is a product of a planned breeding program conducted by the Inventors in Yokaichi-shi, Shiga, Japan. The objective of the breeding program is to create new *Mandevilla* cultivars with large and uniquely colored flowers.

The new *Mandevilla* originated from a cross-pollination made by the Inventors in Yokaichi-shi, Shiga, Japan in February, 2002, of a proprietary selection of *Mandevilla hybrida* identified as code number MH-7, not patented, as the female, or seed parent with a proprietary selection of *Mandevilla hybrida* identified as code number M37-1, not patented, as the male, or pollen, parent. The cultivar Sunparacopapi was discovered and selected by the Inventors as a flowering plant from within the progeny of the stated cross-pollination in a controlled environment in Yokaichi-shi, Shiga, Japan.

Asexual reproduction of the new cultivar by cuttings in Yokaichishi, Shiga, Japan, since October, 2003, has shown that the unique features of this new *Mandevilla* are stable and reproduced true to type in successive generations.

SUMMARY OF THE INVENTION

Plants of the cultivar Sunparacopapi have not been observed under all possible environmental conditions. The phenotype may vary somewhat with variations in environment such as temperature and light intensity without, however, any variance in genotype.

The following traits have been repeatedly observed and are determined to be the unique characteristics of 'Sunparacopapi'. These characteristics in combination distinguish 'Sunparacopapi' as a new and distinct cultivar:

1. Upright and vining plant habit.
2. Medium-sized foliage.

3. Freely flowering habit.
4. Pink-colored flowers.
5. Long flowering period.

Plants of the new *Mandevilla* differ primarily from plants of the female parent selection in flower color as plants of the female parent selection have white-colored flowers. In addition, plants of the new *Mandevilla* have smaller flowers than plants of the female parent selection.

Plants of the new *Mandevilla* differ primarily from plants of the male parent selection in flower color as plants of the male parent selection have red-colored flowers. In addition, plants of the new *Mandevilla* have larger leaves than plants of the male parent selection.

Plants of the new *Mandevilla* can also be compared to plants of the *Mandevilla* cultivar Sunmandecos, disclosed in U.S. Plant Pat. No. 15,202. In side-by-side comparisons conducted in Higashiomi, Shiga, Japan, plants of the new *Mandevilla* differed from plants of the cultivar Sunmandecos in the following characteristics:

1. Plants of the new *Mandevilla* had shorter stems with shorter internodes than plants of the cultivar Sunmandecos.
2. Plants of the new *Mandevilla* had larger leaves than plants of the cultivar Sunmandecos.
3. Plants of the new *Mandevilla* had smaller flowers than plants of the cultivar Sunmandecos.
4. Plants of the new *Mandevilla* had lighter pink-colored flowers than plants of the cultivar Sunmandecos.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

The photograph at the top of the sheet comprises a side perspective view of a typical flowering plant of 'Sunparacopapi' grown in a container.

The photograph at the bottom of the sheet is a close-up view of a typical flower of 'Sunparacopapi'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the late spring in a polyethylene-covered greenhouse in Higashiomi, Shiga, Japan for about five months. During the production of the plants, day temperatures averaged 25° C. and night temperatures averaged 15° C.

Botanical classification: *Mandevilla hybrida* cultivar Sunparacopapi.

Parentage:

*Female, or seed, parent.*—Proprietary selection of *Mandevilla hybrida* identified as code number MH-7, not patented.

*Male, or pollen, parent.*—Proprietary selection of *Mandevilla hybrida* identified as code number M37-1, not patented.

Propagation:

*Type.*—By vegetative cuttings.

*Time to initiate roots.*—About two weeks at 23° C. to 25° C.

*Time to produce a rooted young plant.*—About 40 days at 23° C. to 25° C.

*Root description.*—Fibrous, fleshy; light brown in color.

*Rooting habit.*—Freely branching.

Plant description:

*Form.*—Perennial. Upright and vining plant habit. Vigorous growth habit.

*Plant height.*—About 187.5 cm.

*Lateral branch description.*—Length: About 187.5 cm. Diameter: About 4.4 mm. Internode length: About 2.6 cm. Strength: Strong. Texture: Pubescent. Color: Close to 199A.

Foliage description:

*Arrangement.*—Opposite, simple.

*Length.*—About 12.6 cm.

*Width.*—About 6.5 cm.

*Shape.*—Elliptic.

*Apex.*—Cuspidate.

*Base.*—Cordate.

*Margin.*—Entire.

*Texture, upper and lower surface.*—Pubescent.

*Luster, upper surface.*—Glossy.

*Luster, lower surface.*—Glossy to dull.

*Venation pattern.*—Pinnate, reticulate.

*Color.*—Developing foliage, upper and lower surfaces: Close to 144A. Fully expanded foliage, upper surface: Close to 137A; venation, close to 144B. Fully expanded foliage, lower surface: Close to 146B; venation, close to N170C.

*Petiole length.*—About 1.1 cm.

*Petiole diameter.*—About 3.1 mm.

*Petiole texture, upper and lower surfaces.*—Sparsely pubescent.

*Petiole color, upper and lower surfaces.*—Close to 177B.

Flower description:

*Flower type and habit.*—Single salverform flowers; flowers racemose; flowers face mostly outwardly. Freely flowering habit, about five flowers per inflorescence.

*Natural flowering season.*—Long flowering period; early summer to late autumn in Japan; flowering continuous during this period.

*Flower longevity on the plant.*—About seven to ten days. Flowers not persistent.

*Fragrance.*—Not detected.

*Inflorescence length.*—About 16.6 cm.

*Inflorescence diameter.*—About 11.2 cm.

*Flowers.*—Appearance: Flared trumpet, corolla fused, five-parted; petals imbricate; flowers roughly star-shaped. Diameter: About 8.7 cm. Depth (length): About 8.6 cm. Throat diameter: About 2 cm. Tube length: About 5.4 cm. Tube diameter, mid-section: About 1.8 cm. Tube diameter, base: About 3.6 mm.

*Flower buds.*—Height: About 6.8 cm. Diameter: About 1.2 cm. Shape: Lenticular. Color: Close to 145D.

*Corolla.*—Arrangement/appearance: Single whorl of five petals, fused into flared trumpet; petals imbricate. Petal length: About 3.8 cm. Petal width: About 3.6 cm. Petal shape: Spatulate. Petal apex: Acute. Petal margin: Entire; curled outwardly; slightly undulate. Petal texture, upper and lower surfaces: Smooth, glabrous. Color: Petal, when opening, upper and lower surfaces: Close to 65A. Petal, fully opened, upper and lower surfaces: Close to 65B. Tube: Close to 65D tinted with 150D. Throat: Close to 15A; at the petal lobe, close to 68A.

*Sepals.*—Arrangement/appearance: Five per flower in a single whorl; fused. Length: About 6.5 mm. Width: About 3.4 mm. Shape: Lanceolate. Apex: Acute. Margin: Entire. Texture, upper and lower surfaces: Smooth, glabrous. Color, immature, upper and lower surfaces: Close to 145C; towards the apex, close to 53A. Color, mature, upper and lower surfaces: Close to 145C; towards the apex, close to 53A.

*Peduncles.*—Length: About 5.8 cm. Diameter: About 2.2 mm. Texture: Pubescent. Strength: Flexible, but strong. Color: Close to 144A.

*Pedicels.*—Length: About 1.6 cm. Diameter: About 2.7 mm. Texture: Pubescent. Strength: Flexible, but strong. Color: Close to 145B.

*Reproductive organs.*—Stamens: Quantity/arrangement: Typically five; filaments fused to corolla; anthers, connivent. Anther shape: Elliptic. Anther size: About 8.2 mm by 1.9 mm. Anther color: Close to 12C. Pollen amount: Scarce. Pollen color: Close to 155D. Pistils: Quantity: Typically one. Pistil length: About 2.7 cm. Stigma shape: Conical. Stigma color: Close to 144A. Style length: About 2.2 cm. Style color: Close to 144D. Ovary color: Close to 144B.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 4° C. to about 30° C.

It is claimed:

1. A new and distinct *Mandevilla* plant named 'Sunparacopapi' as illustrated and described.

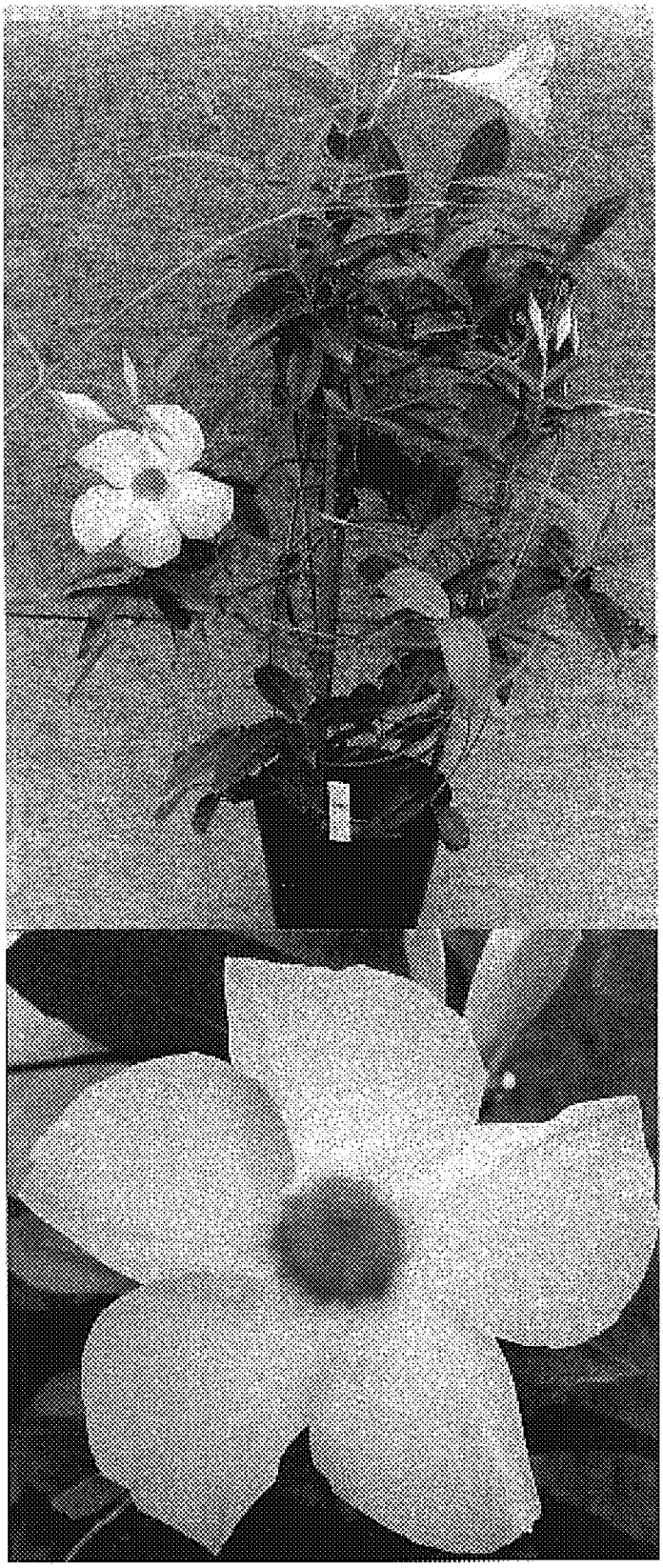

* * * * *